US005667972A

United States Patent [19]

Drmanac et al.

[11] Patent Number: 5,667,972
[45] Date of Patent: Sep. 16, 1997

[54] METHOD OF SEQUENCING OF GENOMS BY HYBRIDIZATION OF OLIGONUCLEOTIDE PROBES

[75] Inventors: Radoje T. Drmanac; Radomir B. Crkvenjakov, both of Beograd, Yugoslavia

[73] Assignee: Hyseg, Inc., Sunnyvale, Calif.

[21] Appl. No.: 461,106

[22] Filed: Jun. 5, 1995

Related U.S. Application Data

[63] Continuation of Ser. No. 45,912, Apr. 12, 1993, Pat. No. 5,492,806, which is a continuation of Ser. No. 723,712, Jun. 18, 1991, Pat. No. 5,202,231, which is a continuation of Ser. No. 175,088, Mar. 30, 1988, abandoned.

Foreign Application Priority Data

Apr. 1, 1987 [YU] Yugoslavia ..................... 570/87

[51] Int. Cl.$^6$ .............................. C12Q 1/68; C07H 21/04
[52] U.S. Cl. ........................ 435/6; 536/23.1; 935/77; 935/78
[58] Field of Search ...................... 435/6; 536/23.1; 935/77, 78

[56] References Cited

U.S. PATENT DOCUMENTS

| | | | |
|---|---|---|---|
| 4,562,159 | 12/1985 | Shafritz | 435/6 |
| 4,591,567 | 5/1986 | Britten et al. | 435/6 |
| 4,613,566 | 9/1986 | Potter | 435/6 |
| 4,672,040 | 6/1987 | Josephson | 435/6 |
| 4,675,283 | 6/1987 | Roninson | 435/6 |
| 4,683,195 | 7/1987 | Mullis et al. | 435/6 |
| 4,683,202 | 7/1987 | Mullis | 435/6 |
| 4,720,786 | 1/1988 | Hara | 435/6 |
| 4,766,062 | 8/1988 | Diamond et al. | 435/6 |
| 4,770,992 | 9/1988 | Van den Engh et al. | 435/6 |
| 4,794,073 | 12/1988 | Dattagupta et al. | 435/6 |
| 4,849,334 | 7/1989 | Lorincz | 435/6 |
| 4,865,967 | 9/1989 | Shiraishi et al. | 435/6 |
| 4,865,968 | 9/1989 | Orgel et al. | 435/6 |
| 4,942,124 | 7/1990 | Church | 435/6 |
| 5,002,867 | 3/1991 | Macevicz | 435/6 |
| 5,149,625 | 9/1992 | Church et al. | 435/6 |
| 5,202,231 | 4/1993 | Drmanac et al. | 435/6 |
| 5,492,806 | 2/1996 | Drmanac et al. | 435/6 |
| 5,525,464 | 6/1996 | Drmanac et al. | 435/6 |

FOREIGN PATENT DOCUMENTS

| | | |
|---|---|---|
| 0 152 886 | 8/1985 | European Pat. Off. |
| 0 197 266 | 10/1986 | European Pat. Off. |
| 3506703 | 10/1986 | Germany |
| 88/01302 | 2/1988 | WIPO |
| 89/10977 | 11/1989 | WIPO |
| 90/03382 | 4/1990 | WIPO |
| 90/04652 | 5/1990 | WIPO |

OTHER PUBLICATIONS

Asseline et al., "Nucleic acid-burning molecules with high affinity and base sequence specificity: Intercalating agents covalently linked to oligodeoxynucleotides," *Proc. Natl. Acad. Sci. USA*, 81:3297–3301 (1984).

Bains and Smith, "A Novel Method for Nucleic Acid Sequence Determination," *J. Theor. Biol.*, 135:303–307 (1988).

Besmer et al., "Hybridization of Polydeoxynucleotides with Tyrosine Transfer RNA Sequences to the r-Strand of 80psu$_{III}$ DNA," *J. Miol. Biol.*, 72:503–522 (1972).

Bilofsky and Burks, "The Gen Bank genetic sequence data bank," *Nucleic Acids Research*, 16:1861–1875 (1988).

Breslauer et al., "Predicting DNA duplex stability from the base sequence," *Proc. Natl. Acad. Sci. USA*, 83:3746–3750 (1986).

Burke et al., "Cloning of Large Segments of Exogenous DNA into Yeast by Means of Artificial Chromosome Vectors," *Science*, 236:806–812 (1987).

Chan et al., "Detection of subpicogram quantities of specific DNA sequences on blot hybridization with biotinylated probes," *Nucleic Acids Research*, 23:8083–8091 (1985).

Collins and Weissman, "Directional cloning of DNA fragments at a large distance from a initial probe: A circularization method," *Proc. Natl. Acad. Sci. USA*, 81:6812–6816 (1984).

Coulson et al., "Toward a physical map of the genome of the nematode *Caenorhabditis elegans*," *Proc. Natl. Acad. Sci. USA*, 83:7821–7825 (1986).

Craig et al., "Molecular Techniques in Mammalian Genetics: A New Era in Genetic Analysis," *Human Genetics*, pp. 126–132 (Vogel and Sperling eds., Springer–Verlag Berlin) (1987).

Craig et al., "Ordering of cosmid clones covering the Herpes simplex virus type I (HSV-I) genome: a test case for fingerprinting by hybridization," *Nucleic Acids Research*, 18:2653–2660 (1990).

(List continued on next page.)

*Primary Examiner*—Stephanie W. Zitomer
*Attorney, Agent, or Firm*—McCutchen, Doyle, Brown & Enersen

[57] ABSTRACT

The conditions under which oligonucleotides hybridize only with entirely homologous sequences are recognized. The sequence of a given DNA fragment is read by the hybridization and assembly of positively hybridizing probes through overlapping portions. By simultaneous hybridization of DNA molecules applied as dots and bound onto a filter, representing single-stranded phage vector with the cloned insert, with about 50,000 to 100,000 groups of probes, the main type of which is (A,T,C,G)(A,T,C,G)N8 (A,T,C,G), information for computer determination of a sequence of DNA having the complexity of a mammalian genome are obtained in one step. To obtain a maximally completed sequence, three libraries are cloned into the phage vector, M13, bacteriophage are used: with the 0.5 kb and 7 kbp insert consisting of two sequences, with the average distance in genomic DNA of 100 kbp. For a million bp of genomic DNA, 25,000 subclones of the 0.5 kbp are required as well as 700 subclones 7 kb long and 170 jumping subclones. Subclones of 0.5 kb are applied on a filter in groups of 20 each, so that the total number of samples is 2,120 per million bp. The process can be easily and entirely robotized for factory reading of complex genomic fragments or DNA molecules.

7 Claims, No Drawings

OTHER PUBLICATIONS

Craig et al., "Relaxation Kinetics of Dimer Formation by Self Complementary Oligonucleotides," *J. Mol. Biol.*, 62:383–401 (1971).

Devlin et al., "Random Peptide Libraries: A Source of Specific Protein Binding Molecules," *Science*, 249:404–406 (1990).

Donis–Keller et al., "A Genetic Linkage Map of the Human Genome," *Cell*, 51:319–337 (1987).

Drmanac et al., "Partial Sequencing By Olig–Hybridization: Concept and Applications in Genome Analysis," *The First International Conference on Electrophoresis, Supercomputing and the Human Genome* (Cantor & Lim eds., World Scientific) (1990).

Drmanac et al., "Reliable Hybridization of Oligonucleotides as Short as Six Nucleotides," *DNA and Cell Biology*, 9:527–534 (1990).

Drmanac et al., "Sequencing of Megabase Plus DNA by Hybridization: Theory of the Method," *Genomics*, 4:114–128 (1989).

Dworetzky, "Opening New Frontiers in Molecular Biology," *Discover*, Mar.:14–15 (1987).

Estivill and Williamson, "A rapid method to identify cosmids containing rare restriction sites," *Nucleic Acids Research*, 15:1415–1425 (1987).

Garza et al., "Physical mapping of complex genomes," *Nature*, 340:577–578.

Gillam et al., "The base–pairing specificity of cellulose–pdT$_9$," *Nucleic Acids Research*, 2:625–634 (1975).

Gingeras and Davis, "Hybridization properties of immobilized nucleic acids," *Nucleic Acids Research*, 15:5373–5390 (1987).

Hadfield, "Chromsome Walking," *Focus*, 5:1–5 (1983).

Hochhauser, "Bringing Biotechnology to Market," *High Technology*, Feb.:55–60 (1983).

Ikuta et al., "Dissociation kinetics of 19 base paired oligonucleotide–DNA duplexes containing different single mismatched base pairs," *Nucleic Acids Research*, 15:797–811 (1987).

Khrapko et al., "An oligonucleotide hybridization approach to DNA sequencing," *FEB*, 256:118–122 (1989).

Kohara et al., "The Physical Map of the Whole E. coli Chromosome: Application of a New Strategy for Rapid Analysis and Sorting of a Large Genomic Library," *Cell*, 50:495–508 (1987).

Latham and Smith, "Detection of Single Base Mutations in DNA Molecules Using the Solution Melting Method," *DNA*, 8:223–231 (1989).

Lewin, "Proposal to Sequence the Human Genome Stirs Debate," *Science*, 232:1598–1600 (1986).

Little et al., "Plasmid Vectors for the Rapid Isolation and Transcriptional Analysis of Human β–Globin Gene Alleles," *Mol. Biol. Med.*, 1:476–488 (1983).

Lochet et al., "Pertussis Toxin Gene: Nucleotide Sequence and Genetic Organization," *Science*, 232:1258–1264 (1986).

Maniatis et al., "Analysis of Recombinant DNA Clones," Molecular cloning, p. 388 (Cold Spring Harbor Laboratory) (1982).

Matthews and Kricka, "Analytical Strategies for the Use of DNA Probes," *Analytical Biochemistry*, 169:1–25 (1988).

Maxam and Gilbert, "A New Method for Sequencing DNA," *Proc. Natl. Acad. Sci. USA*, 74:560–564 (1977).

Maxam and Gilbert, "Sequencing End–Labeled DNA with Base–Specific Chemical Cleavages," *Methods in Enzymology*, pp. 499–560 (Academic Press, Inc.) (1980).

McCafferty et al., "Phage Antibodies: Filamentous Phage Displaying Antibody Variable Domains," *Nature*, 348:552–554 (1990).

Meinkoth and Wahl, "Hybridization of Nucleic Acids Immobilized on Solid Supports," *Analytical Biochemistry*, 138:267–284 (1984).

Midendorf et al., "Large Scale DNA Sequencing," *American Biotechnology Laboratory*, 6:14–21 (1988).

Nasmyth and Sulston, "High–altitude Walking with YACs'" *Nature*, 328:380–381 (1987).

Ohtsuka et al., "An Alternative Approach to Deoxyoligonucleotides as Hybridization Probes by Insertion of Deoxyinosine at Ambiguous Codon Positions," *J. Biol. Chem.*, 260:2605–2608 (1985).

Olson et al., "Random–clone strategy for genomic restriction mapping in yeast," *Proc. Natl. Acad. Sci. USA*, 83:7826–7830 (1986).

Porschke and Eigen, "Co–opertive Non–enzymtic Base Recognition," *J. Mol. Biol.*, 62:361–381 (1971).

Poustka and Lehrach, "Jumping libraries and linking libraries: the next generation of molecular tools in mammalian genetics, " *TIG*, Jul. 174–179 (1986).

Poustka et al., "Molecular Approaches to Mammalian Genetics," *Cold Spring Harbor Symposia on Quantitative Biology*, 51:131–139 (1986).

Prober et al., "A System for Rapid DNA Sequencing with Fluorescent Chain–Terminating Dideoxynucleotides," *Science*, 238:336–341 (1987).

Sanger et al., "DNA sequencing with chain–terminating inhibitors," *Proc. Natl. Acad. Sci. USA*, 73:5463–5467(1977).

Scott and Smith, "Searching for Peptide Ligands with an Epitope Library," *Science*, 249:386–390 (1990)

Smith and Hood, "Mapping and Sequencing the Human Genome: How to Proceed," *Bio/Technology*, 5:933–939 (1987).

Smith et al., "Fluorescence detection in automated DNA sequence analysis," *Nature*, 321:674–679 (1986).

Tapper, "Changing messages in the genes," *New Scientist*, 25:53–55 (1989).

Vizard et al., "A Simplifield Biochemistry for DNA Sequencing," *BioTechniques*, 8:430–437 (1990).

Wallace et al., "Hybridization of synthetic oligodeoxyribonucleotides to 174 DNA: the effect of single base pair mismatch," *Nucleic Acids Research*, 6:3543–3557 (1979).

Wallace et al., "The use of synthetic oligonucleotides as hybridization probes. II. Hybridization of oligonucleotides of mixed sequence to rabbit β–globin DNA," *Nucleac Acids Research*, 9:879–894 (1981).

Wetmur, "Hybridization and Renaturation Kinetics of Nucleic Acids," *Annual Review of Biophysics and Bioengineering*, pp. 337–361 (Mullins ed., Annual Reviews Inc.) (1976).

Wetmur and Davidson, "Kinetics of Renaturation of DNA," *J. Mol. Biol.*, 31:349–370 (1968).

Wood et al., "Base composition–independent hybridization in tetramethylammonium chloride: A method for oligonucleotide screening of highly complex gene libraries," *Proc. Natl. Acad. Sci. USA*, 82:1585–1588 (1985).

Zoler, "Caltech Develops New DNA Sequencing Method," *Bio/Technology*, 3:395–396 (1985).

METHOD OF SEQUENCING OF GENOMS BY HYBRIDIZATION OF OLIGONUCLEOTIDE PROBES

This is a continuation of U.S. application Ser. No. 045,912, filed Apr. 12, 1993, now U.S. Pat. No. 5,492,806; which is a continuation of U.S. application Ser. No. 07/723, 712 filed Jun. 18, 1991, now U.S. Pat. No. 5,202,231; which is a continuation of U.S. application Ser. No. 07/175,088 filed Mar. 30, 1988 now abandoned; which is based on Yugoslavian No. P-570/87 filed on Apr. 1, 1987.

TECHNICAL FIELD

The subject of this invention belongs to the field of molecular biology.

TECHNICAL PROBLEM

Genomes range in size from about $4\times10^6$ base pairs (bp) in *E. coli* to $3\times10^9$ bp in mammals. Determination of the primary structure, i.e., sequence, of the entire human genome, is a challenge of the 20th century. A further challenge for biology is the determination of the entire genomic sequence for characteristic species of the living world. It would allow qualitative progress in explaining the function and evolution of organisms. It would also be a great step forward in the explanation and treatment of many diseases, in the food industry and in the entire field of biotechnology.

STATE OF THE ART

Prior Art

Recombinant DNA technology has allowed the multiplication and isolation of short fragments of genomic DNA (from 200 to 500 bp) whereby a sufficient quantity of material for determination of the nucleotide sequence may be obtained in a cloned fragment. The sequence is determined on polyacrylamide gels which separate DNA fragments in the range of 1 to 500 bp, differing in length by one nucleotide. Distinguishing among the four nucleotides is achieved in two ways: (1) by specific chemical degradation of the DNA fragment at specific nucleotides, in accordance with the Maxam and Gilbert method (Maxam, A. M. and Gilbert, W., 1977, Proc. Natl. Acad. Sci., 74, 560); or (2) utilizing the dideoxy sequencing method described by Sanger (Sanger, F., et al., 1977, Proc. Natl. Acad. Sci., 74, 5463). Both methods are laborious, with competent laboratories able to sequence approximately 100 bp per man per day. With the use of electronics (computers and robots), sequencing can be accelerated by several orders of magnitude. The idea of sequencing the whole human genome has been discussed at many scientific meetings in the U.S.A. (Research News, 1986, Science, 232, 1598–1599). The general conclusion was that sequencing is possible only in big, organized centers (a sequencing factory) and that it would take about 3 billion dollars and at least ten years. For the time being the Japanese are the most advanced in organizing components of one such center. Their sequencing center has the capacity of about 1 million bp a day at the price of about 17¢ per bp (Commentary, 1987, Nature, 325,771–772). Since it is necessary to sequence three lengths of a genome, because of random formation of cloned fragments of about 500 bp, 10 billion bp could be sequenced in approximately 30 years in such a center, i.e., it would take 10 such centers to sequence the human genome in several years.

DESCRIPTION OF THE INVENTION

Our process of sequencing, compared with the existing ones, involves an entirely different logic, and is applicable specifically for determining a sequence of complex DNA fragments and/or molecules (more than 1 million base pairs). It is based upon specific hybridization of oligonucleotide probes (ONPs), having a length of 11 to 20 nucleotides.

Conditions of hybridization of ONPs have been found under which complete homology with the target sequence is differentiated from a single base pair mismatch (Wallace, R. B., et al., 1979, Nucleic Acid Res., 6, 3543–3557). If the method of hybridization with 3M tetramethyl ammonium chloride is used, the melting point of the hybrid is dependent only on the ONP length, not its GC content (Wood, W. L., et al., 1985, Proc. Natl. Acad. Sci. U.S.A., 82, 1585–1588). Thus, hybridization under such conditions unequivocally determines the sequence. Hybridization of genomic DNA multiplied as subclones of convenient length with a sufficient number of ONP's will allow the entire genome to be sequenced with the aid of Computerized assembly of these detected sequences. We believe this method is an order of magnitude quicker and cheaper than technique presently being developed. Therefore, it is more suitable for genomic sequencing of all characteristic species.

In order to apply this method, it is necessary to optimize the length, sequence and number of ONPs, the length and number of subclones and the length of the pooled DNA which may represent a hybridizing sample. Eleven-mer ONPs are the shortest oligonucleotides that can be successfully hybridized. This means a priori that $4^{11}$ (4,194,304) ONPs are needed to detect each sequence. The same number of independent hybridizations would be necessary for each subclone or a pool of subclones. Positively hybridizing ONPs would be ordered through overlapping 10-mers. This results in the DNA sequence of the given subclone.

The process of assembling a subclone sequence is interrupted when the overlapping 10-mer is repeated in the given subclone. Thus, uninterrupted sequences are found only between repeated 10-mers or between longer oligonucleotide sequences (ONSs). These fragments of a subclone sequence (SF) cannot always be ordered in an unambiguous linear order without additional information. Therefore, it is important to determine the probable number of SFs (Nsf) distributed along certain length of DNA; this can be achieved through the application of probability calculations.

The distribution of ONSs along a randomly formed DNA sequence is binomial. The average distance between identical neighboring ONSs (A) depends only on the ONS length (L), and is given as: $A=4^L$. The probability of having ONSs repeated N times in a fragment of the length of Lf bp is given as:

$$P(N,Lf)=C(N,Lf)\times(1/A)^N\times(1-1/A)^{Lf} \quad (1)$$

where C(N,Lf) represents the number of the N class combinations consisting of Lf elements. The expected number of different ONSs having the length L or average distance A, which are repeated N times in a Lf bp fragment, is given as the product $P(N,Lf)\times A$. If a sequence is assembled through the overlapping length L or through average distance Ao, then Nsf in a fragment Lf is represented as:

$$Nsf=1+Ao\times\Sigma N\times P(N,Lf), \quad N\geq 2 \quad (2)$$

If all 11-mers ($4\times10^6$) are used, about 3 SFs are to be expected per Lf of the length of 1.5 kb. We shall return to the problem of ordering SFs later.

The required synthesis of $4\times10^6$ 11-mers, is impracticable for sequencing by hybridization (SBH). However, it is unsuitable to omit a significant number of ONPs (more than 25%), because it leads to gaps in the sequence. A far better way to decrease the number of independent ONP syntheses and of independent hybridizations is to use ordered ONP groups. This method requires sequencing of shorter fragments, but no gaps appear in the resultant sequence. A forty-fold decrease in the number of syntheses and hybridizations requires a seven-fold increase in the number of subclones.

The use of ordered ONP groups, in an informative respect, is the same as using shorter ONPs. For instance, there are 65,536 different 8-mer ONSs. Since 8-mer ONSs, according to the current knowledge, cannot form a stable hybrid, the 11-mer group can be used as an equivalent. In other words, all 11-mers in a group have one 8-mer in common, so that the information obtained concerns only its presence or absence in the target DNA. Each of the anticipated groups of 11-mers contains 64 ONPs of the (N2)N8(N1) type (5'→3' orientation is as written. /Nx/means $\underline{x}$ unspecified bases, and /Ny/ means y specified bases. A sequence can be detected with about 65,000 such groups. If equation (2) is applied, then DNA fragments 200 bp long are expected to have 3 SFs on average. Due to dispersion, some fragments of this length will have 10 and more SFs.

Because of its unrandom GC and dinucleotide composition, ONPs of the (N2)N8(N1) type are not very convenient for sequencing mammalian DNA. The more AT bases contained in the common sequence of an ONP group, the longer it should be. Taking this into account, there remain three types of suitable probes: (N1)N10, where N10 stands for all 10-mers not containing G+C; (N1)N9(N1), where N9 stands for all 9-mers containing 1 or 2 G+C; and (N2)N8(N1), where N8 represents all 8-mers containing 3 or more G+C. About 81,000 such ONP groups are necessary. The average value of their Ao(Aao) is about 30,000. Equal Ao value in random DNA requires about 130,000 ONPs of the (N2)N8(A or T) and (N2)N8(or rG) types. These ONP groups allow sequencing of fragments 300 bp long, with 3 SFs at average. This increase of 25% in the number of syntheses allows a multifold decrease in the number of necessary SCs (see below). Apart from these probes it is necessary to synthesize an additional 20,000 ONPs in Order to (1) solve the problem of repetitive sequences, (2) confirming the ends of inserts and (3) supplementing information lost due to the fact that it is unfeasible to use ONP's which hybridize with vector DNA.

Repetitive sequences, or, generally speaking, ONSs repeated in tandems and having the length of one or more bp (AAAAAAA . . . TCTCTCTC . . . TGATGATG . . . ) represent a problem in sequencing by hybridization. The above mentioned probes cannot determine length of repetitive sequences that are longer than the common part of a ONP group. Therefore, the precise determination of repetitive ONSs up to 18 bp long, that represent the largest part of these ONPs, requires application of the following ONPs: 160 NP An and Tn, where the value of $\underline{n}$ stretches between 11 and 18 bp, ONP (AT), ONP Cn and $G_n$ where $\underline{n}$ is valued from 9 to 18 bp, ONP (AT)n where $\underline{n}$ takes on the values of (12, 14, 16, 18), 25 ONPs (AC)n, (AG)n (TC)n (TG)n and (CG)n, where $\underline{n}$ is valued (10, 12, 14, 16, 18), 60 ONPs of the (N1 N2 N3)n type which encompass all trinucleotides and $\underline{n}$ is (12, 15, 18), 408 ONPs which include all 5-mers in tandems, having the length of 15 and 18 bp, 672 ONPs consisting of 6-mer tandems up to 18 bp long, and 2340 ONPs consisting of 7-mer tandems 18 bp long. The total number of these ONPs is 3725.

In order to confirm the ends of DNA inserts in an subclone, it is necessary to synthesize an additional 2048 ONPs of the N6(N5) and (N5)N6 types, where N6 represents sequences of the vector ends, and (N5) represents all possible 5-mers in both cases.

The problem of the vector DNA can be solved in two ways. One is prehybridization with cold vector DNA shortened for 7 bp at both sides of the cloning site. The other method is to omit ONPs complementary to the vector DNA. Since phage M13 has been chosen as the most suitable phage vector (see below), it would eliminate the use of approximately 7,000 ONPs. This is a significant percentage (11%) if 65,000 ONP's [(N2)N8(N1)] are utilized. It can be decreased to about 3% if, instead of the given 7,000 ONPs, an additional 21,000 ONPs of the (N1)(N°1)N8(N1) type are used, where N8is 7,000 M13 8-mers, and (N°1) represents each of the trinucleotides not present by the given 8-mer.

The calculations, supra, are related to the sequencing of single stranded DNA. To sequence double stranded DNA it is not necessary to synthesize both complementary ONPs. Therefore, the number of necessary ONPs can be halved. Yet, due to advantages of the M13 system, we will discuss further the method of sequencing the single stranded DNA. In this case, gaps of unread sequences will appear in the subclones, because half the ONPs are used. However, a gap in one subclone will be read in the subclone containing the complementary chain. In a representative subclone library each sequence is repeated about 10 times on average. This means that it is probable to have each sequence cloned in both directions, i.e., that it will be read on both DNA strands. This allows the use of uncomplementary ONPs with only an increase in algorithmic computation. Thus, the total number of necessary ONPs would be approximately 50,000. If an M13 vector, able to package both strands either simultaneously or successively could be devised, the use of uncomplementary ONPs would not impose any additional requirement.

All subclone and/or all pools of subclones hybridize with all anticipated ONPs. In this way a set of positively hybridizing s is attained for each subclone, i.e., subclone pool. These ONPs are ordered in sequences by overlapping their common sequences, which are shorter than the ONPs by only one nucleotide. In order to detect overlapping ONPs faster, it is necessary to determine in advance which ONP overlap maximally with each synthesized ONP. Thus, each ONP will obtain its subset of ONPs: (ONPa, ONPb, ONPc, ONPd) 5' ONP×3' (ONPe, ONPf, ONPg, ONPh). Ordering must follow the route of detecting which one out of the four ONPs from the 5' side, and which one out of four from the 3' side positively hybridize with the given subclone, i.e., pool. Assembling continues until two positively overlapping ONPs for the last assembled ONP are found. Thereby, one SF is determined. When all SFs are extended to the maximum, the process is terminated.

The number of SFs is increased for a larger length of DNA by using described ONP groups. Generally, unequivocal ordering can be achieved with 3 SFs per subclone when the SFs are counted in the same way as Nsf is calculated in equation (2). These SFs are recognized as the two placed at the ends of an insert with third placed, logic of SFs cannot be The ordering of SFs cannot be solved for a convenient length of a subclone because it would be too short. Our solution is the mutual ordering of SFs and large numbers of subclones, with the possibility of using subclone pools as one sample of hybridization and/or competitive hybridization of labeled and unlabeled ONPs.

To obtain the maximum extended sequence by SBH on subclones that may be used repeatedly, it is necessary to use three subclone libraries in the M13 vector, with 0.5-7 kb inserts and with inserts of different size, which consist of two sequences: their distance in genomic DNA should be about 100 kb. The first library serves primarily to order SFs. These subclones cannot be preserved for later experimentation. These subclones enter hybridization as pools obtained by simultaneous infection during or after growth of a phage. The second library is the basic one. The subclones it contains are convenient for further use. The length of 7 kbp represents the current limit of the size of an insert suitable for successful cloning in M13. The function of the third library is to regularly associate parts of sequences separated by highly homologous sequences longer than 7 kbp as well as uncloned DNA fragments into an undivided sequence.

Hybridization of subclones of all libraries with ONPs, and computation of SFs is followed by mutual ordering of the SFs and subclones. The basic library is the first to be ordered. Overlapping subclones are detected by the content of the whole or of a part of starting SFs of the starting subclone. Generally, all mammalian SFs having a length of 20 bp or more are suitable. The average SF length of these subclones is calculated on the basis of equation (2) is 12 bp. This means that there are enough SFs of suitable length. Besides, it is known among which SFs—most often there are two—is the one which continues from the starting SF. In this case both sequences are examined; the correct one is among them, and overlapping subclones are detected by it. On the basis of content of other SFs, exact displacement of overlapping subclones in relation to the starting subclone is determined. The linear arrangement of subsets (SSFs) is achieved by detecting of all subclones overlapping with the starting subclone. SSFs are defined by neighboring ends of overlapping subclones (either beginning-beginning, beginning-end or end-end). The process of overlapping subclones is resumed by the SF taken from the jutting SSF of the most jutting subclone. The process of assembling is interrupted when encountered with an uncloned portion of DNA, or, similar to forming of SFs, with a repeated sequence longer than 7 kbp. The maximum size of groups of ordered overlapping subclones 7 bp long is obtained by this method, as well as linear arrangement of the SSFs of their SFs.

The length of DNA contained in a SSF an is fundamental in this procedure. This length depends on the number of SSFs, which is equivalent to the number of subclone ends, i.e., two times the number of subclones. A representative library of DNA fragments of 1,000,000 bp requires 700 SCs of 7 kbp. Therefore, the average size of a SSF is 715 bp. The real average number of SFs within an SSF is not 1/10 the number of SFs in a subclone 7 kbp long nor is it dependent on the length of subclone. Instead, the real number is dependent on the length of an SSF. According to equation (2), for the length of 715 bp and an Aao of 30,000 bp (the values for described ONPs), 16 SFs with an average length of 45 bp are expected on average. The ordering of SFs within obtained SSFs is performed through the 0.5 kb subclone library. This method does not require all subclones to be individual; the use of a subclone pool is sufficient. The subclone in a respective pool are informative if they do not overlap with each other. Informatively and technologically suitable is a 10 kb pool of cloned DNA, although it is not the limit. The number of such necessary subclones or pools is such that the maximum size of an SSF formed by them can be no longer than 300 bp. The ONPs proposed for this length are expected to give 3 SFs (equation 2), which, as explained, may be unequivocally ordered. Utilizing binomial distribution has enabled the derivation of the equation:

$$Nsa = Nsc(1 - 2Nsc/Nbp)^{Lms}$$

where Nsa is the number of SSFs greater than Lms, Nsc is the number of bp per fragment or molecule of the DNA being sequenced, Lms stands for the size of on SSF, which an average gives the number of 3 SF, which can be ordered; in this case it amounts 300 bp. On the basis of this equation it is determined that 25,000 subclones of 0.5 kb are necessary for a DNA fragment 1 million bp long. The number of 10 kb pools is 1250. Average size of an SSF obtained with these subclones is 20 bp.

The ordering of SFs is performed by computer detection of pools containing subclones which overlap with the starting SSF. This detection is performed on the basis of the content of a part of the whole SF, randomly chosen from the starting SSF. Contents of other SFs from the starting SSF determine the overlapping proportion of subclones of 5 kb. Due to their high density, the arrangement of SFs in the starting SSF is also determined. At the end of this process, the sequence of each group of ordered subclones of 7 kb is obtained, as well as information about which pool contains the subclone of 0.5 kb bearing the determined sequence. At a certain small number of loci the sequence will either be incomplete or ambiguous. Our calculations show that on average it is not less than one locus per million bp, including 30% of randomly distributed undetected ONSs. These loci are sequenced by convenient treatments of subclones which bear them, followed by repeated SBH or competitive hybridization with suitably chosen pairs of labeled and unlabeled ONPs or by classical method or by the advanced classical method.

The procedure of competitive hybridization will be explained by the example of the sequence 7 bp long repeated twice. In this case two SFs end and two others begin with the repeating sequence TTAAAGG which is underlined.

5' NNNNNNNNNNNNNCATTAAAAGG3'
5' NNNNNNNNNNNNNCGTTAAAAGG3'
5' TTAAAAGGTACNNNNNNNN3'
5' TTAAAAGGCCGNNNNNNNN3'

Prehybridization wish surplus of an unmarked ONP, e.g., 5'(N2)CATTAAAAG(N1)3', which cannot hybridize with 5'NNCGTAAAAGG3' due to one uncomplementary base prevents one of the labelled ONPs-5' (N2)AAAAGGTAC (N1)3' or 5' (N2)AAAAGGCCG(N1)3'—from the subsequent hybridization. A pair of mutually competing probes defines a pair of SFs which follow one another. This can be confirmed by an alternative choice of a suitable ONP pair. This procedure may be applied on all repeating ONSs having the length of up to 18 bp. In order to use it for the ordering of a multitude of SFs, prehybridization must be separated from hybridization in both time and space. Therefore, the stability of a hybrid with unlabelled ONP is important. If such stability cannot be achieved by appropriate concentrations of ONPs and by choice of hybridizing temperatures, then a covalent link should be formed between a cold ONP and complementary DNA by UV radiation in presence of psoralen. Alternatively, one might use ONPs which carry reactive groups for covalent linking.

The subclones of the third library are used to link the sequenced portions into a uniform sequence of the entire DNA fragment being sequenced. Approximately 170 subclones are required for 1 million bp. These and other numbers calculated for 1 million bp increase linearly with length for longer DNA fragments. Since these subclones contain sequences which are distanced at 100 kbp on average, they allow jumping over repeated or uncloned sequences, the size of which increases up to 100 kb. This is done by detecting which of the two sequenced portions contains sequences located in one subclone from the library.

The experimental requirement of this method is to have the total number of 50,000 ONPs and hybridizations, and 2120 separated hybridizing subclone samples per DNA fragment approximately 1,000,000 bp long.

The libraries described, supra, are made in the phage vector, M13. This vector allows easy cloning of DNA inserts from 100 to 7,000 bp long, and gives high titer of excreted recombinant phage without bacterial cell lysis. If a bacterial culture is centrifuged, a pure phage preparation is recovered. Additionally, the bacterial sediment can be used for repeated production of the phage as long as the bacterial cell pellet is resuspended in an appropriate nutrient media. With the addition of alkali, DNA separates from the protein envelope and is simultaneously denatured for efficient "dot blot" formation and covalent linking to nylon filters on which hybridization is performed. The quantity of DNA obtained from several milliliters of a bacterial culture is sufficient to hybridize one subclone with all the ONPs. A suitable format for cultivation and robot application on filters are plates similar to micro-titer plates, of convenient dimensions and number of wells. Application of DNA subclones on filters is performed by a robot arm. Even the largest genomes can be satisfactorily sequenced by a robot arm supplied with 10,000 uptake micropipets. After the DNA solution has been removed from the plates, the micropipets are positioned closer to each other by a mechanism reducing the distance between them to 1 mm. The quantity of DNA suitable for 10,000 subclones is then applied to the filter simultaneously. This procedure is repeated with the same 10,000 subclones as many times as necessary. The same procedure is then repeated with all other subclones, their groups numbering 10,000 each. The number of "imprints" of one such group with 50,000 ONPs is approximately 1,000, since each filter can be washed and reused 50 times.

The hybridization is performed in cycles. One cycle requires at maximum one day. All the subclones are hybridized with a certain number of ONPs in one cycle. In order to have the hybridization completed within a reasonable period, an experiment in each cycle should require approximately 1,000 containers, each with one ONP. For the purpose of saving ONPs, a smaller volume of hybridizing liquid is used, and therefore filters are added in several turns. Filters from all hybridizing containers are collected in one container, and are simultaneously processed further i.e., they are washed and biotin is used for labelling of ONPs instead of radioactive particles, colored reactions are developed. All subclones required for sequencing (up to 10 kb in length) can be hybridized in containers with the dimensions 20×20× 20 cm without having to repeat individual cycles.

Hybridization sequencing of fragments cloned in plasmid vectors can be performed one of two ways: by (1) colony hybridization or (2) "dot blot" hybridization of isolated plasmid DNA. In both cases, 2,000 or 3,000 different ONPs in the vector sequence will not be utilized, i.e., will not be synthesized.

Colony hybridization is presumably faster and cheaper than "dot blot" hybridization. Moreover, colony hybridization requires specific conditions to annul the effect of hybridization with bacterial DNA. The marking of probes giving high sensitivity to hybridizations should be done in order to reduce the general background and to allow use of minimal number of bacterial colonies. Marking of ONPs should, however, be via biotinylization, for the benefit of easy and lasting marking in the last step of synthesis. The sensitivity attained (Al-Hakin, A. H. and Hull, R., 1986, Nucleic Acid Research, 14:9965–9976) permits the use of at least 10 times fewer bacterial colonies than standard protocols.

In order to avoid "false positive" hybridization caused by homology of ONP with a bacterial sequence, and in order to use short probes such as 11-mers, which are repeated twice on average in the bacterial chromosome, plasmid vectors that give the maximum number of copies per cell should be used. High copy plasmid vectors, such as pBR322, are amplified to 300–400 copies per bacterial cell when grown in the presence of chloramphenicol. (Lin Chao, S. and Bremer, L., 1986, Mol. Gen. Genet., 203, 150–153). Plasmids pAT and pUC have at least twice the efficiency of multiplication (Twigg, A. J. et al., 1987, Nature, 283, 216–218). Therefore, we can assume that under optimal conditions even 500 copies of plasmid per bacterial cell can be attained. The additional sequences within the hymeric plasmids will surely cause a decrease in plasmid copies per cell, especially in the presence of poisonous sequences. Therefore, operations should be performed with about 200 copies of chimeric plasmid per bacterial cell. This means that, an average, the signal would be 100 times stronger with every 11-mer if there is a complementary sequence on the plasmid as well. That is sufficient difference for hybridization with bacterial DNA not even to be registered, when a small quantity of DNA (i.e., small colonies) is used.

Using a binomial distribution we determined how many ONPs will be repeated more than 10 times in bacterial chromosomes due to random order. Such ONPs will give unreliable information or cannot be used at all if they give signals of approximate strength to signals of all colonies.

Results obtained by using equation (1), supra, where Lf is the length of bacterial chromosome of $4\times10^6$ bp, and A the number of different ONPs, are shown in Table 1.

This calculation assumes that all nucleotides and dinucleotides occur in equal quantities in DNA of E. coli, which is almost completely the case.

TABLE 1

| Number of repetitions | Probability of a certain frequency of 11-mers in the genome of E. coli | | | | | | |
|---|---|---|---|---|---|---|---|
| | 0 | 2 | 4 | 6 | 8 | 10 | 14 |
| Percentage of 11-mers | 13.5 | 27 | 9 | 1.2 | 0.086 | 0.004 | $7 \times 10^{-6}$ |
| Number of all 11-mers | — | — | — | — | 1720 | 80 | 0.14 |

Table 1 shows that the repetition of any 11-mer greater than 13 times cannot be expected, and that the total number of those repeated more than 10 times is about 300. Therefore, the majority of 11-mers will have a greater than 20 times stronger signal, which is due to the cloned DNA, than the one due to the bacterial DNA. Naturally, a certain number of 11-mers will be very frequent in bacterial DNA due to functional reasons, but, since bacteria do not allow any higher degree of repetitiveness, due to their capability to recombine, it can be expected that the number of such 11-mers will be small. They would simply not be used for hybridization.

The problem of hybridization with bacterial DNA can also be solved by selective prehybridization if "cold" bacterial DNA is used. By preparing this DNA in fragments larger than 100 bp and smaller than approximately 10,000 bp under stringent hybridization conditions (where only the fragments with homology larger than 50 bp hybridize), the bacterial DNA would preferentially be "covered", since there is an insignificant chance for random homologous sequences between bacterial and eukaryotic DNA 50 bp long, and more, to exist.

The selective prehybridization in the sequencing method allows the use of more probes at the same time by means of colony hybridization. The necessary number of independent hybridizations can thus be reduced. On the other hand, in order to know which ONP (ONPs) permit the combination to hybridize positively, every probe must be found in more combinations, which increases the necessary mass of every ONP. But, if it is necessary to attain a certain concentration of probe in the hybridization liquid for successful and quick hybridization, and since the probe is minimally spent and the concentration is, therefore, insignificantly reduced after the hybridization, there is a possibility of adding a larger number of filters into the same hybridization liquid, thereby reducing the quantity of necessary probe(s).

By using 30 ONPs per one hybridization and by repeating one ONP in three combinations, where none of 90 other probes is found in two or three combinations (on account of triple the necessary mass of every ONP), a ten-fold reduction in number of hybridizations is achieved. On the basis of probability that a combination of a certain number of ONPs hybridize with a fragment of genomic DNA of a certain length, we determined the percentage of information being lost in relation to the separate use of every ONP.

The average distance of homologous sequences for 30 ONPs of 11 nucleotides in length is approximately 130,000 bp. For sequencing of mammalian genomes, in order to provide more accurate reading, a proportionally greater number of ONPs having a more frequent homologous sequence (i.e., containing more A and T bases), would be synthesized in order that the average distance "A" would in this case be approximately 100,000 bp. The probability that the combination of 30 ONPs will hybridize with a fragment of genomic DNA having the length of Lf=5,000 bp was determined using the equation $P(Lf)=1-(1-1/A)^{Lf}$. In this case, P=0.0485. The probability that three different combinations will hybridize with the same fragment is $1.25 \times 10^4$. Since 2 million colonies (fragments) are hybridized, in about 250 colonies all three combinations with one common ONP will hybridize with at least one of their probes. We will not know whether these colonies will have the sequence complementary to the common ONP. Since the number of colonies which contain at least one complementary sequence ONP common for these combinations, for mammalian genomes, is from 300 to 3,000, the number of colonies that will hybridize at the same time with a common probe will, in the worst case, be less than 4. For a million different ONPs a maximum of 4,000,000 information units are rejected if we suppose that the common ONP does not hybridize when we are not sure whether it does or does not. This results in the loss of only 1/1,000,000 part of information obtained from the separate hybridization with every ONP.

A greater possibility of information loss lies in rejecting the positive hybridization when there is an ONP common for three combinations which hybridize with the specific genomic fragment due to a wrong determination that there is at least one ONP in every combination which hybridizes with the specific fragment. Such errors occur in determining the positive hybridization for every ONP in three observed combinations, while observing whether the other two combinations in which they are present hybridize or not. If the other two combinations hybridize, there is a great chance that the positive hybridization comes from the common ONP. But, if the combinations are large, the chance that the two different probes hybridize in one combination each is great. That would mean that the common ONP probably does not hybridize, and so the initially observed ONP should not be rejected as the one that does not hybridize with the specific fragment. This probability (Pgi) can approximately be calculated by using the equation $Pgi=\{[P(lf)]^2 \times K\}^3$, where K is the number of ONPs in the combination, and P(lf) is the probability that at least one of K ONPs hybridize on one fragment of the genomic DNA of length Lf (equation (1), supra). The formula is valid for $P(Lf)^3 \times K<1$. When the fragments of length Lf=5,000 bp are sequenced, 0.1% of information is lost with K=30 ONPs, 0.5% with K=40 ONPs, 1.32% with K=45 ONPs, 3.3% are lost with K=50 ONPs and 16% of information is lost with K=60 ONPs. We can conclude that the reduction of necessary number of hybridizations of 10 to 15 times can be attained with small information loss. The necessary quantity of filters would also be 10–15 times less, such as the number of replicas to be made out of 2 million clones.

The total number of hybridization points can also be reduced with the use of large combinations in several steps of hybridization. On account of 2–3 thousand additional hybridizations and two or three rearrangements of hybridizational points, every dot could thus be searched with about 3 to 4 times less hybridizations (i.e., so many fewer instances of application to the filter would be required).

Hybridization of isolated plasmid DNA would make the hybridization method easier, but this requires the isolation of a large quantity of plasmid DNA from many clones. The number of clones with fragments of 5,000 bp each for the triple covering of the mammalian genome is $2 \times 10^6$. The necessary quantity of DNA (Mp) from every clone is specified in the equation:

$$Mp=(Dp/DONP) \times Bh \times (1/Br) \times Md$$

DP is the size of the chimeric plasmid in bp, DONP is the length of ONP, Bh is the number of rehybridizations of the same filter, and Md is the mass of DNA which can be detected in the process of hybridization. If we take the most probable values—for DP=8,000, DONP=11, $Bh=2 \times 10^4$, Br=10, and Md=0.1 pg, we find that it is necessary to isolate about 0.2 mg of DNA of every hymeric plasmid. A successful hybridization of filters hybridized with biotinylated probe has not been developed yet. On the other hand there are indications that it is possible to detect even 1/1000 of pg with the biotinylated probes. Therefore, from each of $2 \times 10^6$ clones 0.1 mg ought to be isolated.

Amplification of the whole genomic DNA can be done in about a million portions of up to 10,000 bp, whereby the genome would be covered more than three times. This can be achieved with the use of a suitable mixture of oligonucleotides as primers. With 50,000 different oligonucleotides that have about 800 repeated complementary sequences in the unrepetitive portion of mammalian genomes (say a 12-mer with C+G from 1–5) a million amplified reactions with combinations of 50 primers each can be performed, such that every primer combines with every other primer only once. With such combinations of primers on 60 loci within the genome, there will be on average two primers in such orientation such that their 3' ends are facing, and are at a distance shorter than 300 bp. Fragments limited by those primers will amplify. Since their average length is about 150 bp, the total length of the amplified genome is about 9,000 bp. A million of such amplification reactions replaces the plasmid or phage library of a mammalian genome. In the amplification, the primers that enter the highly repetitive sequences (those that repeat more than 2–3,000 times) cannot be used, and therefore only sequencing of unrepetitive portions of the genome would be performed. Besides, with 50,000 primers at a frequency of 800 times per unrepetitive portion of the genome, about 10% of the unrepetitive portion of the genome would not enter the amplification units. With the use of 100,000 primers only, 0.1% of the unrepetitive part of the genome would not amplify. With 100,000 primers it is necessary to perform 4 million amplification reactions.

Using the dot blot hybridization of amplification reactions with oligonucleotides serving as primers and newly synthesized ONPs up to the necessary number of about 1 million, only the sequences of amplified fragments would be read, since, with the amplification of $2 \times 10^4$ times, every ONP with the complementary sequence in the amplified fragment would have from 3 to 1,000 times greater number of targets than when it hybridizes with the homologous sequences found only within the non-amplified portion of the genome. A signal 3 times stronger is expected for ONPs 11 nucleotides long which do not contain C or G, and 1,000 times stronger than the 12-mers without A or T. In this analysis it is obvious that for the sequences of regions rich with A or T the ONP longer than 11 bp can be used (12-mer would give a signal 10 times stronger than the background, and there is no possibility of selective prehybridization.

After each cycle of hybridization, the technological procedure is continued by reading of results of hybridization. Data are stored in the memory of the computer center. Data have binary characters (+,-) and are read from several sensitivity thresholds. Based on these, SFs are first formed, and it is followed by mutual ordering of SFs and subclones. At the end of processing of all the data, the computer center determines which subclones must be treated experimentally and what type of treatment should be applied in order to obtain the complete sequence.

SBH is the method which minimizes experimental work at the expense of additional computer work. The only technological requirement is the sequence-specific hybridization of ONP. An incapability to use up to 6% of predicted ONPs can be tolerated, with a prevention of appearance of gaps in reading of a DNA sequence. In order to decrease the number of falsely negative hybridizations (unsuccessful hybridization of ONPs, since their limiting hybridizing length is up to 11 nucleotides), and to eliminate falsely positive ones, predicted ONPs have unspecific bases at the ends, which are practically the only place where faults may appear. Instead of the (N3)N8 type, (N2)N8(N1) groups of ONPs anticipated for measuring of repetitive sequences are synthesized in the form of the ONP group also: (N1)Nx(N1). In the case of some basic ONP groups which give many falsely negative matches, ONP groups of the (N2)N8(N2) type are used, with hybridization at the temperature characteristic for 11-mer ONPs.

Forming of internal duplexes in DNA bound to the filter is one of the recognized structural reasons, which can produce falsely negative matches, i.e., gaps, in reading of a sequence. This problem can be overcome by improved binding of DNA to nylon filters and by fragmentation of DEA prior to applying on a filter (ultrasound, acid, endonucleases) in fragments of average size of 50 bp. A significant number of recombinant molecules will be cut inside the duplex structure, thus preventing its formation and making accurate hybridization possible.

Solutions upon which this method is based enable one to obtain enough data in an entirely automated, computer-guided plant from data in the form of binary signals; computing generates the sequence of complex, cloned DNA fragments and/or molecules, respectively.

On the basis of the introduced sequencing method a factory for sequencing of DNA can be built we believe that a large scientific and technological market for genomic sequences and sequenced genomic fragments of at least 50 characteristic species will be formed.

Except that the existence of such a factory is economically justified, it would, in a relatively short period of time, enable a great number of scientists to, instead of cloning and sequencing of certain genes with less efficiency, study the functions of fragments of genomic DNA of known sequence and create new, useful combinations of genetic material, using the method of genetic engineering.

We claim:

1. A method of determining the sequence of an ambiguous locus in a nucleic acid fragment in a sequencing by hybridization process, said method comprising:

(a) prehybridizing said nucleic acid fragment with an excess of unlabeled first oligonucleotide probe which is exactly complementary to one possible sequence at said ambiguous locus;

(b) competitively hybridizing said nucleic acid fragment with a labeled second oligonucleotide probe which is exactly complementary to a second possible sequence at said ambiguous locus;

(c) detecting whether the labeled second oligonucleotide probe hybridizes, thereby determining the sequence of said ambiguous locus in said nucleic acid fragment.

2. The method of claim 1, wherein step (b) is repeated with other labeled second oligonucleotide probes which are exactly complementary to other possible sequences at said ambiguous locus.

3. The method of claim 1, further comprising the step of forming a covalent link between the complementary sequence and the unlabeled first probe that is hybridized to the complementary sequence in the nucleic acid fragment.

4. The method of claim 3, wherein the covalent link is formed by exposing the unlabeled first probe hybridized to the complementary sequence in the nucleic acid fragment to psoralen in the presence of ultraviolet radiation.

5. The method of claim 1, wherein said oligonucleotide probes are 8-mers to 20-mers.

6. The method of claim 1, wherein said oligonucleotide probes are 11-mers.

7. A method for ordering a plurality of fragments of a subclone nucleic acid sequence having ambiguous loci at their ends, comprising the steps of:

(a) prehybridizing subclone nucleic acids with an excess of an unlabeled oligonucleotide probe at least part of which is exactly complementary to a portion of an ambiguous locus at a first end of one of the fragments;

(b) competitively hybridizing the subclone nucleic acid with a labeled oligonucleotide probe which is exactly complementary to a portion of an ambiguous locus at a first end of another of the fragments, wherein a portion of the labeled oligonucleotide probe sequence at an end of the labeled oligonucleotide probe is the same as the sequence at an end of the unlabeled oligonucleotide probe;

(c) detecting whether the labeled second oligonucleotide probe hybridizes;

(d) repeating steps (a)-(c) with combinations of other unlabeled and labeled oligonucleotide probes until the order of the fragments of the nucleic acid sequence can be determined.

* * * * *